(12) United States Patent
Bargatin et al.

(10) Patent No.: US 7,555,938 B2
(45) Date of Patent: Jul. 7, 2009

(54) THERMOELASTIC SELF-ACTUATION IN PIEZORESISTIVE RESONATORS

(75) Inventors: Igor Bargatin, Pasadena, CA (US); Jessica L. Arlett, Pasadena, CA (US); Michael L. Roukes, Pasadena, CA (US); Inna Kozinsky, Pasadena, CA (US); John Sequoyah Aldridge, Carlsbad, CA (US); Edward B. Myers, Sherman Oaks, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 11/857,615

(22) Filed: Sep. 19, 2007

(65) Prior Publication Data

US 2008/0068000 A1 Mar. 20, 2008

Related U.S. Application Data

(60) Provisional application No. 60/845,807, filed on Sep. 19, 2006.

(51) Int. Cl.
*G01R 19/00* (2006.01)
*H01L 21/00* (2006.01)

(52) U.S. Cl. .................... 73/64.53; 73/19.03; 73/24.01; 73/24.06; 324/76.11

(58) Field of Classification Search ................ 73/19.03, 73/24.01, 24.06, 64.53
See application file for complete search history.

(56) References Cited

U.S. PATENT DOCUMENTS

| 6,593,731 | B1 | 7/2003 | Roukes et al. |
| 6,722,200 | B2* | 4/2004 | Roukes et al. ................. 73/580 |
| 2004/0244488 | A1* | 12/2004 | Tang et al. .................... 73/579 |
| 2006/0257286 | A1* | 11/2006 | Adams .................... 422/82.01 |

OTHER PUBLICATIONS

International Search Report for International Application No. PCT/US2007/078886, Report completed Aug. 4, 2008, Report mailed Aug. 15, 2008, 2 pgs.

* cited by examiner

*Primary Examiner*—Daniel S Larkin
(74) *Attorney, Agent, or Firm*—Kauth, Pomeroy, Peck & Bailey LLP (57) ABSTRACT

Systems and methods for thermally actuating piezoresistive cantilevers are described. One embodiment includes a nanoelectromechanical resonator connected in at least one location to a substrate, an electrically conductive path formed on the resonator and a signal source connected to the electrically conductive path and configured to provide an oscillating actuation signal capable of exciting a resonant mode in the resonator.

23 Claims, 11 Drawing Sheets

THERMOELASTIC SELF-ACTUATION IN PIEZORESISTIVE RESONATORS

CROSS-REFERENCE TO RELATED APPLICATIONS

The present application claims priority to U.S. Provisional Patent No. 60/845,807 entitled "Thermoelastic self-actuation in silicon-doped piezoresistive cantilevers" to Bargatin et al., filed Sep. 19, 2006.

STATEMENT OF FEDERALLY SPONSORED RESEARCH

The U.S. government has certain rights in this application pursuant to grant no. F49620-02-1-0085 awarded by the Air Force Office of Scientific Research (AFOSR).

FIELD OF THE INVENTION

The present invention relates to nanoelectromechanical oscillators and more specifically to systems and methods for driving nanoelectromechanical resonators into oscillation using a time-varying application of thermal energy.

BACKGROUND

Micro- and nanomachined cantilevers can be used in a variety of detection applications. involving the detection of a mass. When the mass is present, an oscillating cantilever physically or chemically absorbs or adsorbs the mass. The chemical absorption or adsorption of the mass changes the mass of the cantilever, which is observable as a change in the resonant frequency of the cantilever.

The application of micro- and nanomachined cantilevers in detection processes is ever expanding. U.S. Pat. No. 6,593,731 entitled "Displacement Transducer Utilizing Miniaturized Magnet and Hall Junction" to Roukes et al. discloses the use of nanoelectromechanical (NEMS) cantilevers in force detected magnetic resonance imaging. U.S. Pat. No. 6,722,200 entitled "Apparatus and Method for Ultrasensitive Nanoelectromechanical Mass Detection" to Roukes et al. discloses the use of NEMS cantilevers in mass spectroscopy. U.S. Patent Publication 2004/0244488 entitled "On-Chip Magnetic Force Actuation of Microcantilevers by Coplanar Coils" to Tang et al. describes biofunctionalized microcantilever arrays in hybrid semiconductor-microfluidics devices for the analysis and detection of biological analytes.

SUMMARY OF THE INVENTION

Systems and methods for driving nanoelectromechanical resonators into oscillation using a time-varying application of thermal energy in accordance with embodiments of the invention are disclosed. In many embodiments, the resonators are excited to oscillate out of plane. In several embodiments, the resonators are excited to oscillate in-plane.

One embodiment of the invention includes a substrate, a nanoelectromechanical cantilever connected to a substrate in at least one location, a current path defined proximate the cantilever and a signal source connected via circuitry to the current path. In addition, the signal source is configured to provide a signal to thermally actuate a resonant mode in the cantilever.

In a further embodiment, the nanoelectromechanical cantilever is a bi-layer cantilever.

Another embodiment also includes a base layer and a piezoresistive layer formed on the surface of the base layer.

In a still further embodiment, one end of the bi-layer cantilever is connected to the substrate via a first cantilever leg and a second cantilever leg.

In still another embodiment, the current path includes the piezoresistive layer of the bi-layer cantilever.

In a yet further embodiment, the circuitry includes a pair of symmetric bias resistors that are connected between the signal source and the piezoresistive material in the legs of the bi-layer cantilever.

Yet another embodiment also includes detection circuitry configured to detect variations in the resistance of the piezoresistive layer of the bi-layer cantilever.

In a further embodiment again, the base layer is silicon and the piezoresistive layer is p-doped silicon.

In another embodiment again, the bi-layer cantilever includes a base layer and a metallic circuit trace formed on the base layer, which forms part of the current path.

A further additional embodiment also includes detection circuitry configured to detect variations in the resistance of the metallic circuit trace.

In another additional embodiment, the base layer includes silicon carbide and the circuit trace includes metallic gold.

A still yet further embodiment includes a doubly-clamped nanoelectromechanical beam, a first current path formed on one end of the doubly-clamped beam, and a signal source connected to the first current path via circuitry and configured to provide a signal capable of exciting resonance in the beam.

In still yet another embodiment, the doubly-clamped beam includes a base layer, a first metallic circuit trace formed on the surface of the base layer at one end of the doubly-clamped beam, which forms part of the first current path, and a second metallic circuit trace formed on the surface of the base layer at the other end of the doubly clamped beam, which forms part of a second current path.

A still further embodiment again also includes detection circuitry connected to the second current path and configured to detect actuation of the beam using downmixing detection.

In still another embodiment again, the base layer includes silicon carbide and the metallic circuit traces include metallic gold.

A still further additional embodiment includes a substrate, a beam that includes a channel connected to the substrate by at least two springs, a current path passing through the beam and a signal source connected to the first current path via circuitry and configured to provide a signal capable of exciting in plane resonance in the beam.

In still another additional embodiment, the beam is constructed from a base layer and a metallic surface layer.

In a yet further embodiment again, the base layer includes silicon nitride and the metallic surface layer includes metallic gold.

In yet another embodiment again, the beam is formed from a thin layer of metal.

An embodiment of the method of the invention includes forming a membrane in a silicon on insulator wafer, growing a doped silicon layer, patterning electrodes, forming a membrane, removing an oxide layer and defining resonators.

Another further embodiment includes a nanoelectromechanical resonator connected in at least one location to a substrate, an electrically conductive path formed on the resonator and a signal source connected to the electrically conductive path and configured to provide an oscillating actuation signal capable of exciting a resonant mode in the resonator.

In still another further embodiment, the nanoelectromechanical resonator is a bi-layer cantilever.

In yet another further embodiment, the nanoelectromechanical resonator is a doubly-clamped beam.

In another further embodiment again, the nanoelectromechanical resonator is a beam including a channel connected to the substrate in two locations.

DETAILED DESCRIPTION OF THE INVENTION

Turning now to the drawings, piezoresistive sensors in accordance with embodiments of the invention are illustrated. In many embodiments, the piezoresistive sensors include at least one piezoresistive cantilever or a doubly-clamped beam including layers possessing differing coefficients of thermal expansion. When thermal energy is used to actuate the cantilever, the differing coefficients of thermal expansion create stress within the piezoresistive cantilever and cause the cantilever to bend. Variations in resistance of piezoresistive materials in the piezoresistive cantilever can also be used to detect displacement of the piezoelectric cantilever. In several embodiments, an electrical current is passed through a resistance proximate the piezoresistive cantilever to actuate the piezoresistive cantilever. In other embodiments, the actuation and detection are accomplished using the same piezoresistor. In many embodiments, the piezoresistive cantilever is driven to oscillate by application of an alternating current at the resonant frequency of the cantilever or at half the resonant frequency of the cantilever.

In a number of embodiments, the piezoresistive sensors include doped silicon piezoresistive cantilevers that utilize shared drive and detection lines. In many instances, the piezoresistive cantilevers are constructed from membranes in Silicon on Insulator (SOI) wafers using any of a variety of micro or nanomachining processes. In several embodiments, the piezoresistive sensors utilize drive and detection lines that are separated. In many embodiments, the piezoresistive sensors include at least one metallic piezoresistive cantilever. In other embodiments, the piezoresistive sensors include a doubly-clamped piezoresistive beam.

Thermal Actuation of a Piezoresistive Cantilever

Figure 1:
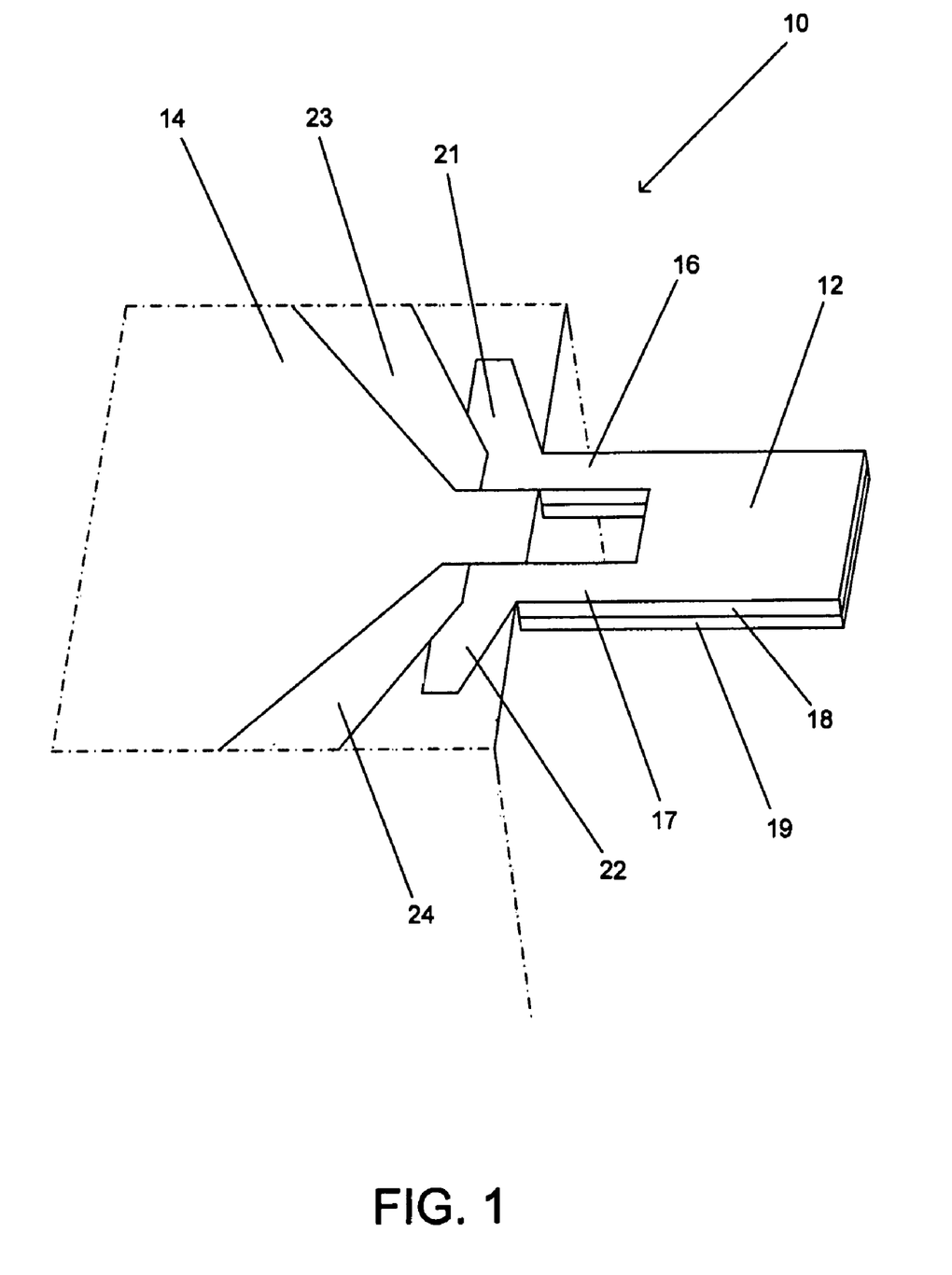
FIG. 1 illustrates a nanoelectromechanical (NEMS) doped silicon piezoresistive cantilever in accordance with an embodiment of the invention.

A piezoresistive sensor including a thermally actuated doped silicon piezoresistive cantilever in accordance with an embodiment of the invention is shown in FIG. 1. The piezoresistive sensor 10 includes a piezoresistive cantilever 12 connected in at least one location to a substrate 14. In the illustrated embodiment, the piezoresistive cantilever 12 is attached to the substrate via two legs 16, 17 that serve to concentrate strain and current in the same region to increase the sensitivity of the device. The piezoresistive sensor 10 includes a surface region of piezoresistive p-doped silicon 18 formed on a base of silicon 19. The surface region of piezoresistive p-doped silicon includes a first contact area 21 on the substrate 14, extends along the first cantilever leg 16, covers the entire upper surface of the cantilever 12, extends along the second cantilever leg 17 and includes a second contact area 22. The surface region of piezoresistive p-doped silicon forms a current path with a resistance determined by the semiconducting material used to form the region. An electrical connection exists between a first circuit trace 23 formed on the substrate 14 and the first contact area 21 of the surface area of piezoresistive p-doped silicon. An electrical connection also exists between a second circuit trace 24 formed on the substrate 14 and the second contact area 22 of the surface area of piezoresistive p-doped silicon.

Thermal Actuation

In the illustrated embodiment, thermal actuation of the cantilever can be achieved by passing an electrical current through the surface area of piezoresistive p-doped silicon. When an electric current flows through the piezoresistive p-doped silicon, the resistance of the piezoresistive p-doped silicon causes heat generation. The piezoresistive p-doped silicon and the base layer of silicon possess different coefficients of thermal expansion. In addition, since the resistive heating is confined to the top doped layer, the temperature of the doped layer and the base layer will often vary differently in time. Therefore, heat generated by an electric current causes the piezoresistive p-doped silicon and the base silicon layers to expand at different rates. The resulting stresses can cause the cantilever to bow. As discussed above, many embodiments utilize narrow cantilever legs to concentrate current flow and stresses. The concentration of stresses within the cantilever legs increases the cantilever displacement that results from the application of an electrical current.

Figure 2:
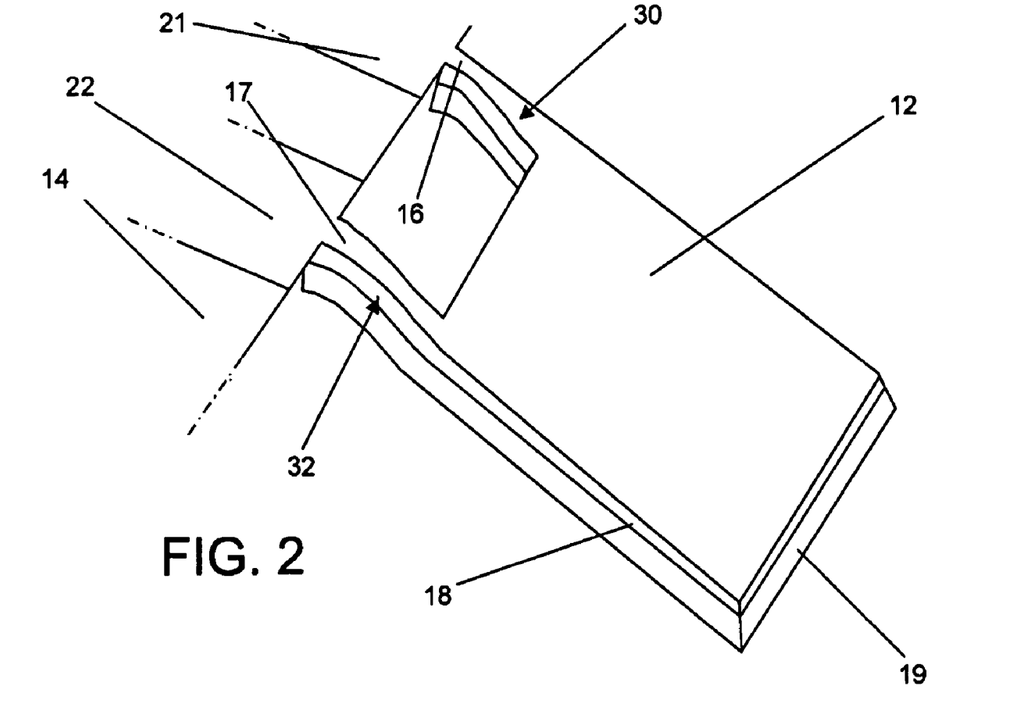
FIG. 2 illustrates a nanoelectromechanical (NEMS) doped silicon piezoresistive cantilever bending in response to thermal actuation in accordance with an embodiment of the invention.

A piezoresistive sensor including a thermally actuated piezoresistive cantilever is illustrated in FIG. 2. The resistance of the current path defined by the surface area of piezoresistive p-doped silicon tends to be highest in the cantilever legs 16, 17, therefore, heat generated by an electric current tends to be greatest in the region of the cantilever legs. In the illustrated embodiment, an electric current flows along a path defined by the first contact area 21, the first cantilever leg 16, the surface 18 of the cantilever 12, the second cantilever leg 17 and the second contact area 22. The generation of heat in the cantilever legs 16, 17 is conceptually illustrated by arrows 30, 32. The heating of the cantilever legs has caused stresses within the cantilever legs associated with the mismatch of the coefficients of thermal expansion and/or the temperatures of the layers of material used in the construction of the cantilever legs. As a result of the stresses, the cantilever legs are bent and the cantilever is displaced from its neutral position.

Drive Circuitry

Piezoresistive cantilevers in accordance with embodiments of the invention can be thermally actuated using electric currents. When a sinusoidal current is applied to the surface region of piezoresistive material, then the resulting surface stresses are also sinusoidal. As will be discussed further below, the cantilever will resonate when actuated by an AC sinusoidal waveform having a frequency equal to the cantilever's resonant frequency or one half of the cantilever's resonant frequency.

Figure 3:
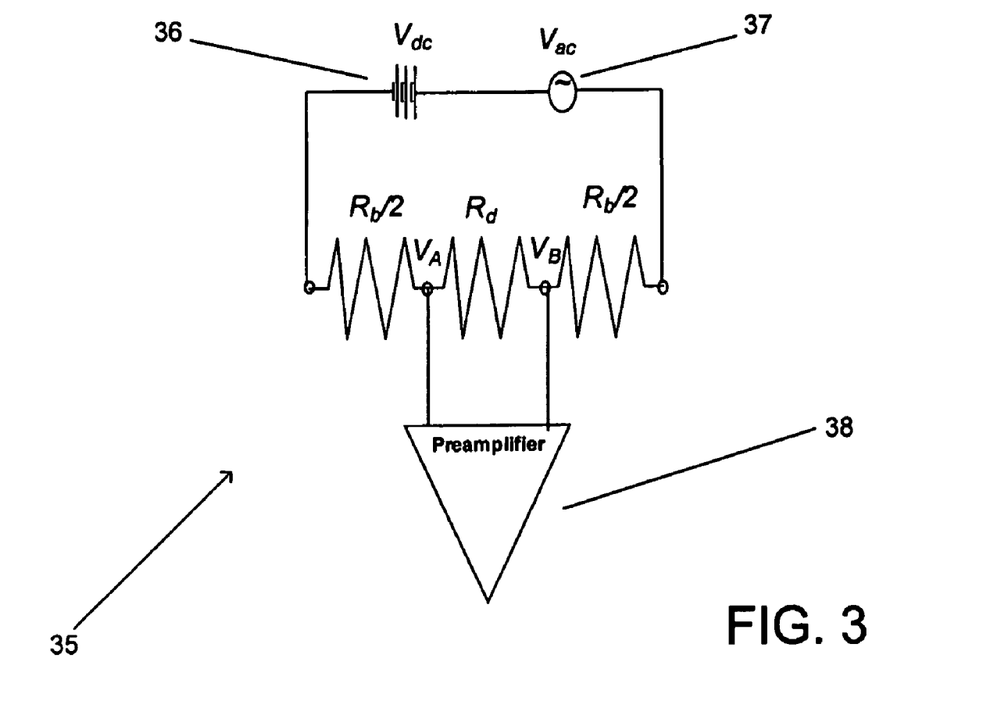
FIG. 3 illustrates an equivalent electrical circuit to a piezoresistive cantilever in accordance with an embodiment of the invention.

A circuit diagram of drive circuitry used to apply a sinusoidal actuation signal to a piezoresistive cantilever in accordance with an embodiment of the invention is shown in FIG. 3. The circuit 35 includes a DC source 36 connected in series with an AC source 37, which generate a DC voltage ($V_{dc}$) to which an AC sinusoidal waveform ($V_{ac}\cos(\omega t)$) is superimposed. The signal generated by the two sources is applied to a series of resistors. The two resistors $R_b/2$ and $R_b/2$ are symmetric bias resistances that apply a bias resistance $R_b$. The resistor $R_d$ represents the resistance of the piezoresistive cantilever and includes a DC resistance component $R_{d_o}$ and a variable resistance component $\delta R_d$, representing the variation in the resistance the piezoresistive materials in the cantilever due to the stresses applied to the cantilever during thermal actuation.

A symmetrical distribution of bias resistances is provided so that the distal end of the cantilever is at ground. Such a configuration can be advantageous where minimizing capacitive interaction between the cantilever and its environment is desirable such as in applications involving mass detection within fluids. In other embodiments, a single bias resistance is used. A single bias resistance can be desirable when a preamplifier used in detection circuitry cannot be AC coupled to the cantilever (e.g. for low frequency measurements). The use of a single bias resistance enables the elimination of the DC bias voltage at the preamplifier input.

Detecting Actuation

During actuation, the thermal expansion of the piezoresistive surface layer 18 of the piezoresistive cantilever leads to surface strain in the device that can be measured as a change in the resistance of the piezoresistive materials used in the construction of the cantilever. In the electric circuit shown in FIG. 3, a preamplifier 38 is connected across the piezoresistive cantilever. The preamplifier 38 can be used to detect variations in the voltage across the cantilever. As discussed above, stresses associated with the thermal actuation of the cantilever alter the resistance of the piezoresistive materials. The following is a discussion of the manner in which the variations in resistance due to thermal actuation can be modeled.

To first order, surface strain resulting from thermal actuation (and measured resistance change) is proportional to the temperature increase associated with the thermal actuation. For small power levels the device temperature is in turn linearly proportional to the power of the actuating signal, which depends on the square of the applied voltage. This discussion implies that:

$$\delta R_d = \beta_1 v^2$$

where $\beta_1$, is a constant of proportionality and v is the voltage drop across the piezoresistive cantilever.

In many embodiments, a DC source and an AC source are used to apply a voltage $V=V_{dc}+V_{ac}\cos(\omega t)$ across the piezoresistive device and one or more bias resistances. To order $\delta R_d$ the measured voltage across the piezoresistive device can be approximated as follows:

$$v = V_A - V_B = \frac{V}{R_b + R_d} R_d = I_b R_{d_o} + \alpha_R I_b \delta R_d$$

where $R_{d_o}$ is the unstrained device resistance and the following parameters were defined to simplify the appearance of the equations:

$$I_b = V/(R_{d_o} + R_b)$$
$$\alpha_R = R_b/(R_{d_o} + R_b)$$

All terms of order $\delta R_d^2$ or greater have been dropped.

Using the expression provided above for $\delta R_d$, the following expression for v can be obtained:

$$v = \frac{1 - (1 - 4 I_b^2 \alpha_R \beta_1 R_{d_o})^{1/2}}{2 I_b \alpha_R \beta_1} - I_b R_{d_o} + 2 I_b^3 R_{d_o}^2 \alpha_R \beta_1$$

The first term gives a DC offset and background at frequency ω. Since $I_b=V/(R_d+R_b)$ and $V=V_{dc}+V_{ac}\cos(\omega t)$, the second term will give contributions at dc, ω, 2ω, 3ω. These are summarized in Table 1, where the signal's Lorentzian line shape is contained within the parameter $\beta_1$.

TABLE 1

Expected harmonics excited through thermal actuation

| Harmonic | Background | Signal | |
| --- | --- | --- | --- |
| | | In phase component | Out of phase component |
| DC | $\frac{R_{d_o}}{R_{d_o}+R_b} V_{dc}$ | $\frac{2 R_{d_o}^2 R_b}{(R_{d_o}+R_b)^4}\left(V_{dc}^3 + \frac{3}{2} V_{dc} V_{ac}^2\right)\beta_1$ | |

TABLE 1-continued

Expected harmonics excited through thermal actuation

| | | Signal | |
|---|---|---|---|
| Harmonic | Background | In phase component | Out of phase component |
| $\omega$ | $\dfrac{R_{d_o}}{R_{d_o}+R_b}V_{dc}$ | $\dfrac{3R_{d_o}^2 R_b}{2(R_{d_o}+R_b)^4}V_{ac}^3 \beta_I$ | $\dfrac{6R_{d_o}^2 R_b}{(R_{d_o}+R_b)^4}V_{dc}^2 V_{ac}\beta_I$ |
| $2\omega$ | | $\dfrac{3R_{d_o}^2 R_b}{(R_{d_o}+R_b)^4}V_{dc}V_{ac}^2 \beta_I$ | |
| $3\omega$ | | $\dfrac{R_{d_o}^2 R_b}{2(R_{d_o}+R_b)^4}V_{ac}^3 \beta_I$ | |

Mechanical Resonance

Figure 4:
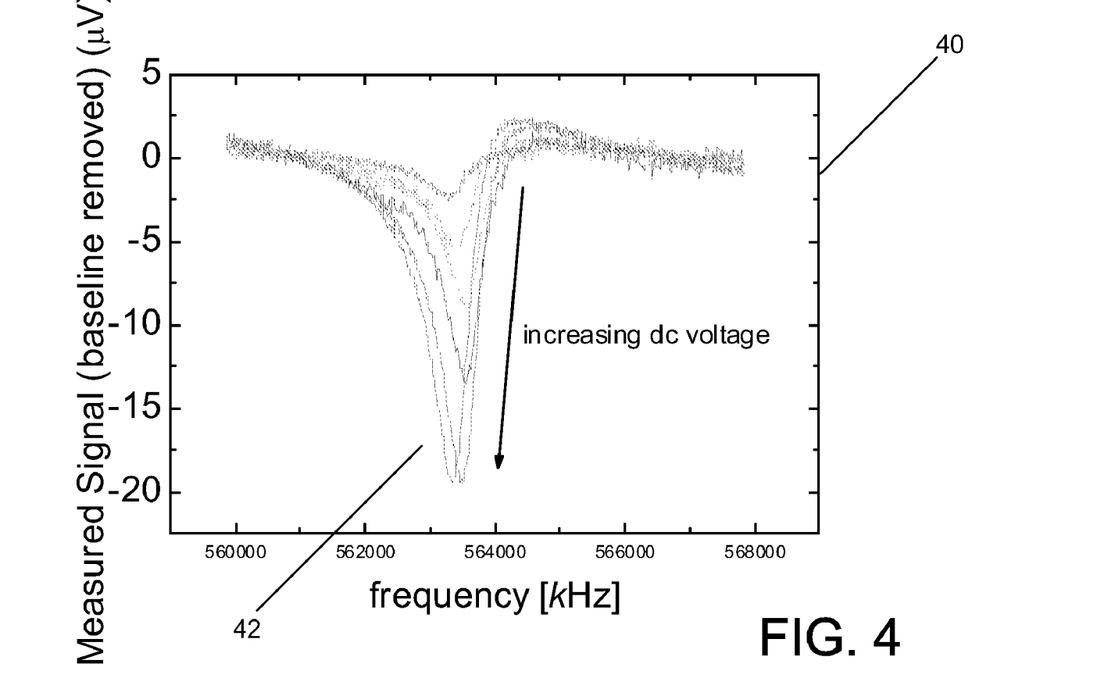
FIG. 4 is a chart illustrating the relationship between the frequency of an AC signal used to thermally actuate a doped silicon piezoresistive cantilever and a signal generated by a transducer configured to detect variations in resistance of piezoresistive materials used in the construction of the cantilever.
Figure 5:
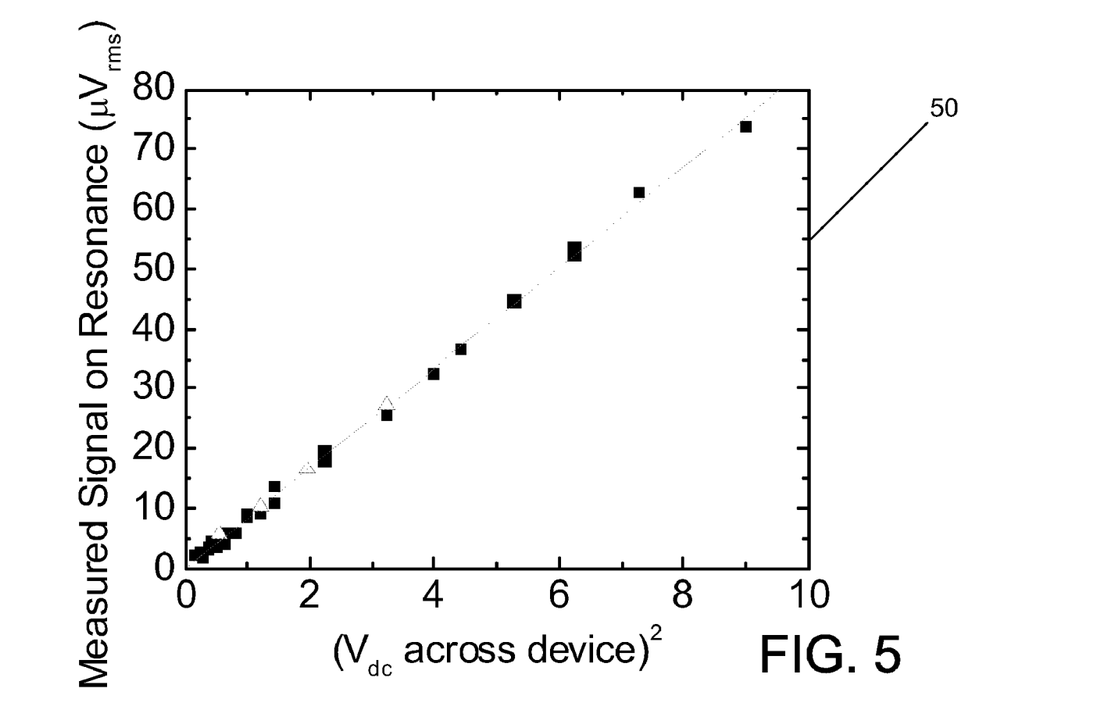
FIG. 5 is a chart illustrating the relationship between the DC voltage across a piezoresistive cantilever and the amplitude of a signal generated by a transducer as the piezoelectric cantilever oscillates at its resonant frequency.

Resonance in a piezoresistive sensor thermally actuated at its first harmonic in accordance with an embodiment of the invention is illustrated in FIGS. 4 and 5. The data was obtained with respect to a piezoelectric sensor including a piezoelectric cantilever having a resonant frequency of 563 kHz. The static resistance of the piezoresistive cantilever was 20 kΩ and symmetric bias resistors had resistances of 6.2 kΩ. A chart showing measurements of voltage across the piezoelectric sensor as the frequency of the actuation signal is increased around the sensor's resonant frequency and as the DC voltage of the actuation signal is increased is illustrated in FIG. 4. The chart 40 includes a number of sets of measurements obtained at different DC voltages. In each instance, the amplitude of the measured voltage peaks 42 at a frequency around 563 kHz. The chart also illustrates that the amplitude of the measured voltage signal at the resonant frequency increases with the magnitude of the DC component of the actuation signal. The relationship between the DC component of the actuating signal and the amplitude of the measured signal is further illustrated in FIG. 5. The graph 50 compares the magnitude of the DC component of the actuation signal with the measured peak voltage at the resonant frequency and indicates that the magnitude of the measured signal scales as $V_{dc}^2$.

Manufacturing Piezoresistive Cantilevers

Figure 6:
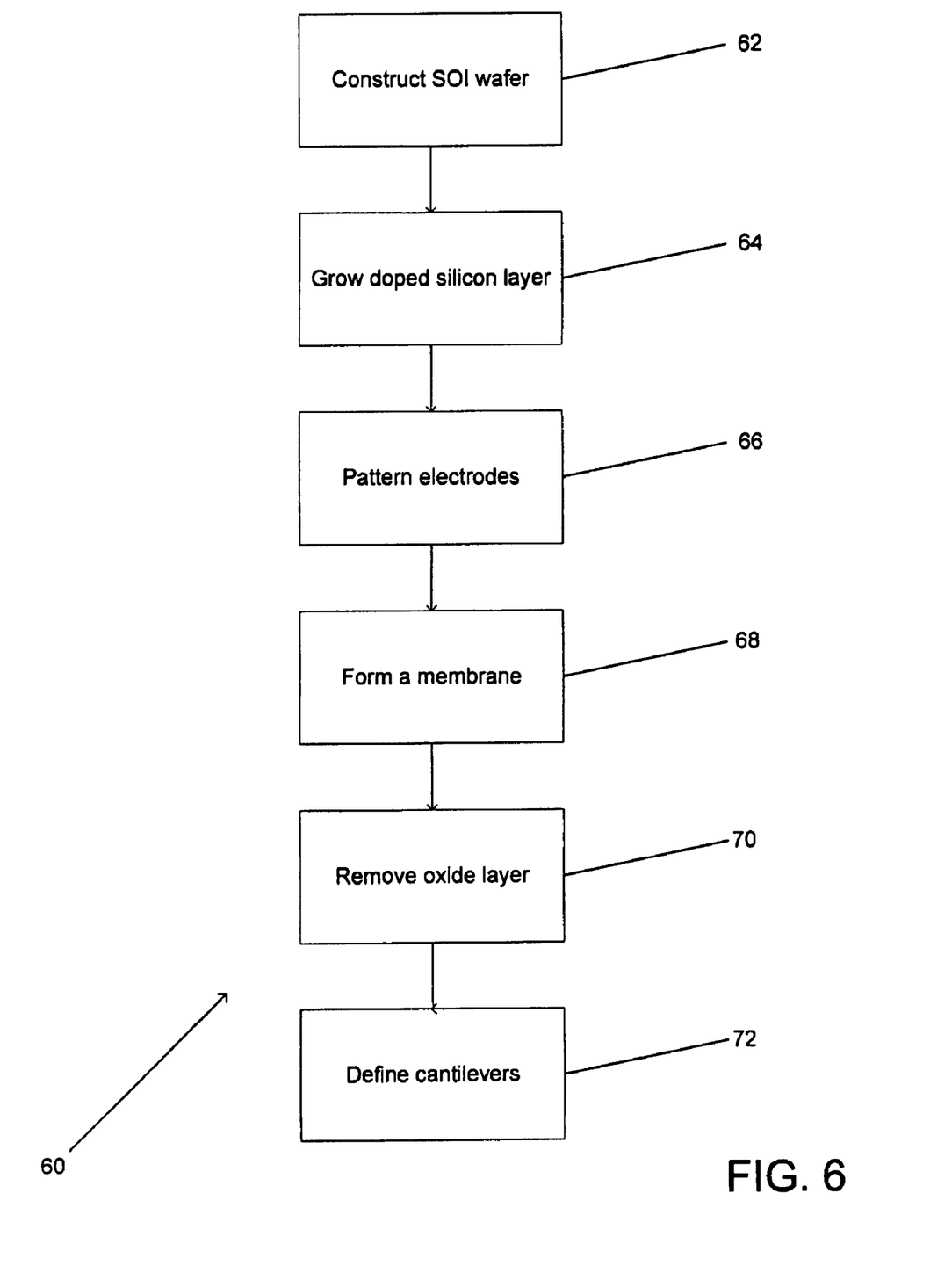
FIG. 6 is a flow chart illustrating a process for constructing a piezoresistive cantilever in accordance with an embodiment of the invention.

A variety of techniques can be used to manufacture nanocantilevers in accordance with embodiments of the invention. A process for manufacturing a nanocantilever in accordance with an embodiment of the invention is shown in FIG. 6. The process 60 commences (62) with the construction of a bonded silicon on insulator (SOI) wafer. SOI wafers are commercial three layer products that typically include a lower silicon layer (referred to as the handle wafer for bonded SOI), a central oxide layer (referred to as the "buried oxide"), and a top silicon layer (referred to as the transducer layer). There are two options for the purchase of these wafers: SiMox material or "bonded" wafers. The choice of a SIMOX wafer or a "bonded" wafer typically depends upon the requirements of a specific application. Examples of suitable SOI wafers include 8" thin (<200 nm) bonded wafers provided by S.O.I. Tech of Bernin, France, which can be further thinned through oxidation and a hydrofluoric acid wet etch and SiMox provided by Ibis Technology Corporation of Danvers, Mass. In many embodiments, a SOI wafer is used that includes a 100 nm thick structural layer of undoped silicon, beneath which is a 750 nm sacrificial layer of silicon dioxide ($SiO_2$). In other embodiments, the composition of the SOI wafer is dependent upon the requirements of the application including the desired mechanical requirements of the piezoresistive cantilevers.

A layer of doped silicon is grown (64) on the structural layer of undoped silicon. In several embodiments, a 30 nm thick layer of boron doped silicon is epitaxially grown on the structural layer with a boron doping level of $4\times10^{19}$ $cm^{-3}$. Organizations that are capable of epitaxially growing a required doped silicon layer include Lawrence Semiconductor Research Laboratory, Inc. of Tempe, Ariz. In many embodiments, other materials can be used in the formation of a piezoresistive surface layer and/or the thickness of the surface layer is determined based upon the requirements of the application.

Metal electrodes are then patterned (66) on the surface of the doped silicon to create an Ohmic contact to the doped silicon epilayer. In many embodiments, the electrodes are constructed using an initial chromium underlayer (typically 5 nm thick) to promote adhesion on which a gold electrode is patterned (typically 60 nm thick).

A membrane is then formed (68) from which the cantilever devices are subsequently patterned. In a number of embodiments, the membrane is formed by performing a deep reactive ion etch (DRIE) on the backside of the substrate that is carefully terminated at the oxide layer. In a typical embodiment, a deep trench in formed in the substrate using the DRIE process having a cross section of, for example, 75 μm×75 μm. An example of an appropriate DRIE process is the Bosch DRIE process, which includes two alternating processes. The two processes are deposition of a passivating layer (typically $C_4F_8$) and exposure to an etching plasma. When the Bosch DRIE process is used, care is required to ensure no passivation remains at the bottom of the trench (which would interfere with oxide removal). In other embodiments, other DRIE processes can be used or other etching processes, such as a KOH wet etch.

The oxide layer is then removed (70) from the backside of the trench. In several embodiments, the oxide layer is removed using a buffered oxide etch. In many embodiments a wet etch is used. Application of a wet etch process is non trivial since the aspect ratio of the trenches makes wetting difficult. It is possible to accomplish this as a wet etch by using ethanol (typically with 95% purity) to wet the wafer. Cyclic heating (to 65° C.) and cooling of the solution can then be used to drive the air out of the via and into the ethanol. The wafers can then be immersed in a de-ionized water bath to displace the ethanol and then placed in undiluted BOE for eight minutes to remove the buried oxide layer. In other embodiments, a hydrofluoric acid (HF) vapor etch is used. This is accomplished by placing the device in HF solution at a concentration of 17% for six minutes (the front side of the device was protected with photoresist). Without the use of the above heating/cooling technique, the air remaining in the trenches prevents the liquid etching solution from entering the vias. However, the HF vapor is able to enter the vias and etch the buried oxide via the following reaction pathway:

$SiO_2+2H_2O\rightarrow Si(OH)_4$ $Si(OH)_4+4HF\rightarrow SiF_4+4H_2O$

Once the oxide layer has been removed, cantilevers are then defined (72). In a number of embodiments, electron beam lithography is used to define the cantilevers. When electron beam lithography is used in the construction of the cantilevers, an aluminum mask (typically 30 nm thick) is used to protect the active areas during the subsequent vertical electron cyclotron resonance plasma etch process (using the gases $NF_3$, $Cl_2$ and Ar) to define the devices. The aluminum mask can be removed using a 10% potassium hydroxide solution. Surface based micromachining is a commonly employed technique that can be used as an alternative to membrane based fabrication of NEMS and MEMS devices. In the latter procedure the oxide under the device is removed from the top, undercutting the device and leaving a suspended structure.

As discussed above, many embodiments of the invention include a geometry that is somewhat more complex than a simple cantilever, they are attached to the supports by two cantilever legs. Using the construction techniques described above, devices can be constructed including cantilevers having a variety of dimensions, such as thickness=130 nm, length=55 µm, width=7 µm and cantilever legs with length=5 µm, width=2 µm. The processes described above can also be used to manufacture much smaller devices including devices on the sub −100 nm scale.

Metallic Piezoresistive Devices

The embodiments described above are bi-layer cantilever structures in which a silicon base layer is combined with a depleted silicon epitaxial layer. A variety of other bi-layer cantilever structures can be used in accordance with embodiments of the invention. In a number of embodiments, piezoresistive sensors are constructed that use a piezoresistive metallic layer instead of a doped semiconductor layer. In many instances, cantilever thickness can be significantly reduced by the substitution of a piezoresistive metallic layer for a doped silicon epitaxial layer.

Figure 7:
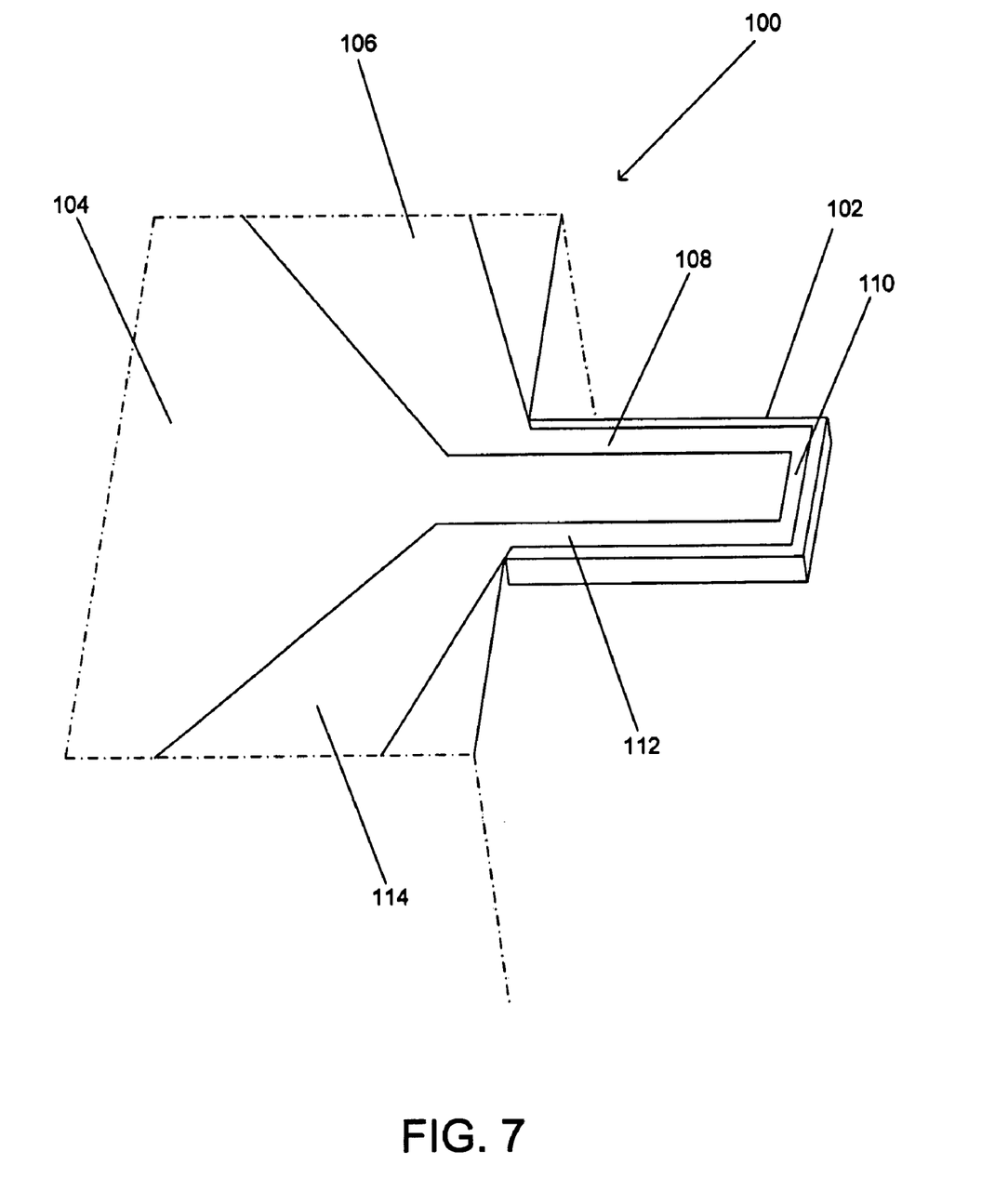
FIG. 7 illustrates a metallic piezoresistive cantilever in accordance with an embodiment of the invention.

An embodiment of a piezoresistive sensor that includes a piezoresistive metallic layer is shown in FIG. 7. The piezoresistive sensor 100 includes a silicon cantilever 102 extending from a substrate 104. The sensor also includes a circuit trace formed on its surface using a piezoresistive material. The surface trace includes a first contact 106 that is connected to a current loop formed by a first length 108 extending along one of the transverse edges of the cantilever, a second length 110 extending along the distal end of the cantilever and a third length 112 extending along the opposite transverse edge of the cantilever. The third length 112 is connected to a second contact 114. In a manner similar to that described above, thermal actuation of the bi-layer cantilever can be achieved by applying a signal across the contacts of the current loop. In addition, modifications in the resistance of the current loop resulting from stresses in the conductors used to construct the current loop can be measured to detect the thermal actuation of the cantilever. In a number of embodiments, the circuit trace is constructed from gold.

In the illustrated embodiment, the metallic pattern formed on the cantilever to create a bi-layer device is patterned in the form of a loop. In many embodiments, a variety of other circuit patterns are used. The nature of the circuit pattern typically depends upon the intended application of the piezoresistive sensor.

Manufacturing of Metallic Piezoresistive Cantilevers

In many embodiments, a metallic piezoresistive sensor can be constructed using a single crystal silicon carbon (3C—SiC) thin film. Resonators such as cantilevers can be constructed by application of multiple aligned steps of e-beam lithography, thin film evaporation, lift-off and reactive plasma etching. Thin metal film loops can then be patterned onto the cantilever using thermally evaporated gold patterned onto a chromium adhesion layer (typically 2 nm thick). In other embodiments, other manufacturing processes suitable for fabricating micro and nano features from a silicon carbon thin film (or other appropriate material) are used in the manufacture of a metallic piezoresistive sensor.

Use of Separate Drive and Detection Circuits

The circuitry used to actuate a piezoresistive cantilever and the circuitry used to detect the actuation of a piezoresistive cantilever can be combined in a single circuit as is described above. Alternatively, the circuits can be separated.

Figure 8:
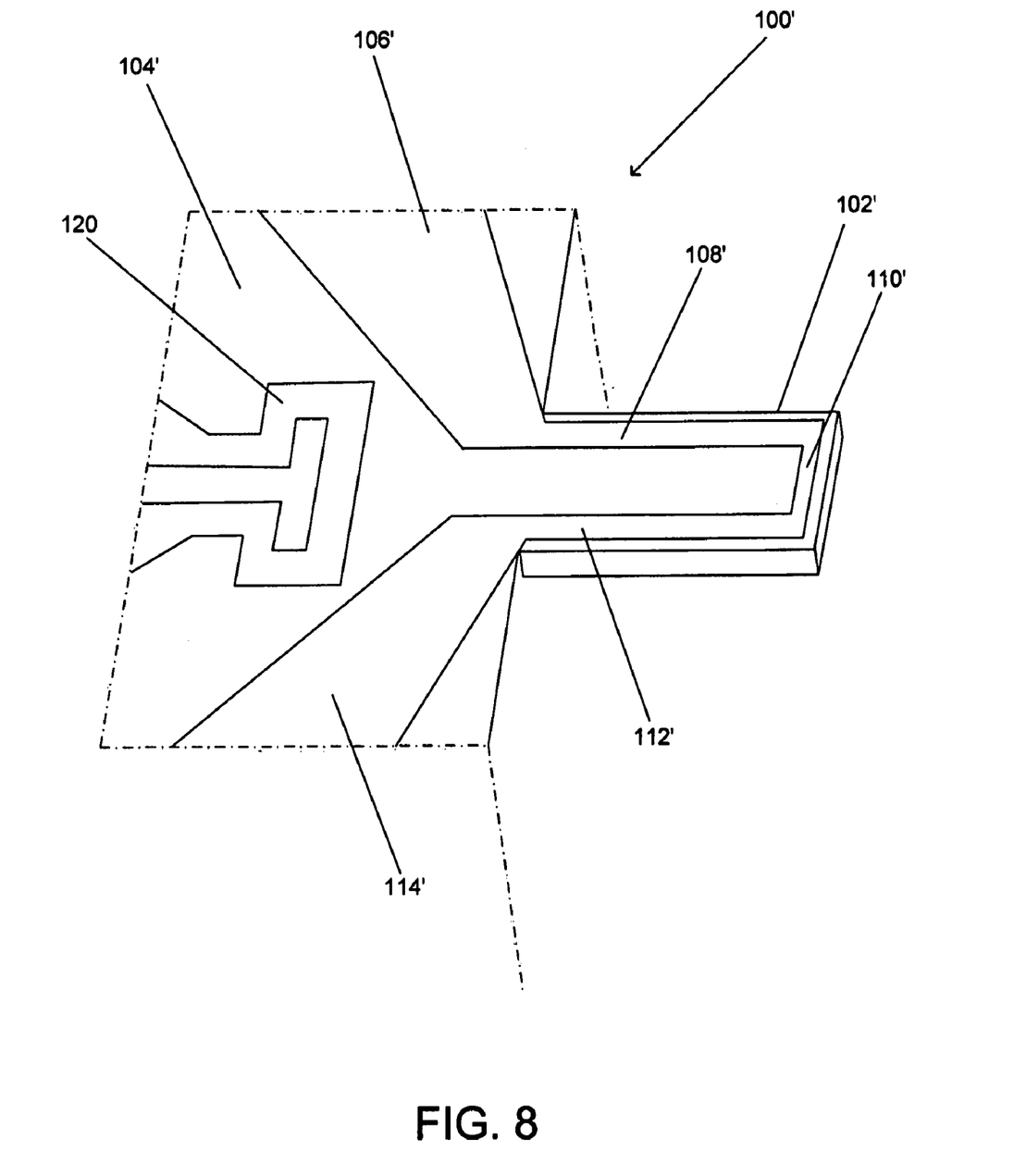
FIG. 8 illustrates a metallic piezoresistive cantilever that includes separate drive and detection lines in accordance with an embodiment of the invention.

An embodiment of a piezoresistive sensor that uses a piezoresistive metallic layer and includes separate drive and detection circuits is shown in FIG. 8. The piezoresistive sensor 100' is similar to the piezoresistive sensor 100 shown in FIG. 7 with the exception that a second circuit trace 120 is provided. The second circuit trace 120 is formed in a loop. Instead of providing an actuation current across the contacts 106' and 114', the actuation current is provided to the second circuit trace 120. As current passes through the current loop, the resistance of the current loop results in the generation of heat. As the bi-layer cantilever is heated, the differences in the coefficients of thermal expansion of the two layers results in the cantilever bending and stresses being applied to the metal in the first circuit trace. A detection current is provided to the first circuit trace via the contacts 106' and 114' enables measurement of the resistance of the first circuit trace. As stresses are applied to lengths 108', 112' of the first circuit trace, the resistance of the first circuit trace changes. As discussed above, the changes in resistance are indicative of the displacement of the cantilever.

Figure 9:
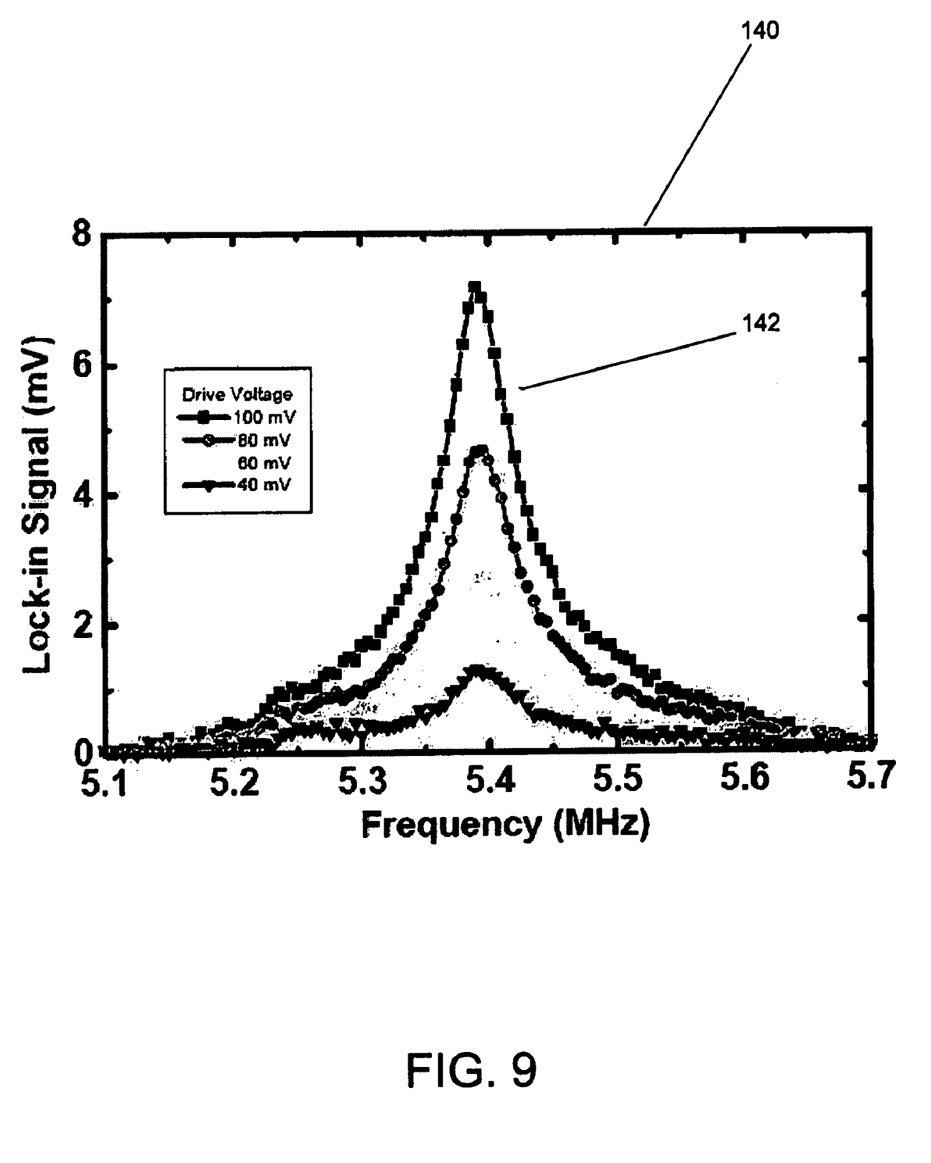
FIG. 9 is a chart illustrating the relationship between the frequency of an AC signal applied to a drive line to actuate a metallic piezoresistive cantilever and the amplitude of a signal generated by a transducer configured to detect variations in the resistance of piezoresistive materials used in the construction of the cantilever.

A chart showing the relationship between the frequency of an actuation signal and the resonant displacement signal of a piezoresistive cantilever similar to the device shown in FIG. 8 is illustrated in FIG. 9. The chart 140 shows a number of voltage measurements taken as the frequency of the actuation signal increases around the resonant frequency of the piezoresistive cantilever. In each instance, a voltage peak 142 is detected at a frequency that is slightly less than 5.4 MHz. The chart also illustrates that increasing the DC component of the actuation signal increases the magnitude of the magnitude of the observed peak voltage at the resonant frequency of the piezoresistive cantilever.

A constant background signal, accounting for approximately 30% of the total signal, was subtracted from the measurements shown in FIG. 9. The background signal is primarily due to heat-induced changes in the resistance of he piezoresistive sensing layer and can be reduced by further optimizing the heater and sensor geometry.

Use of Doubly-Clamped Beams

Figure 10:
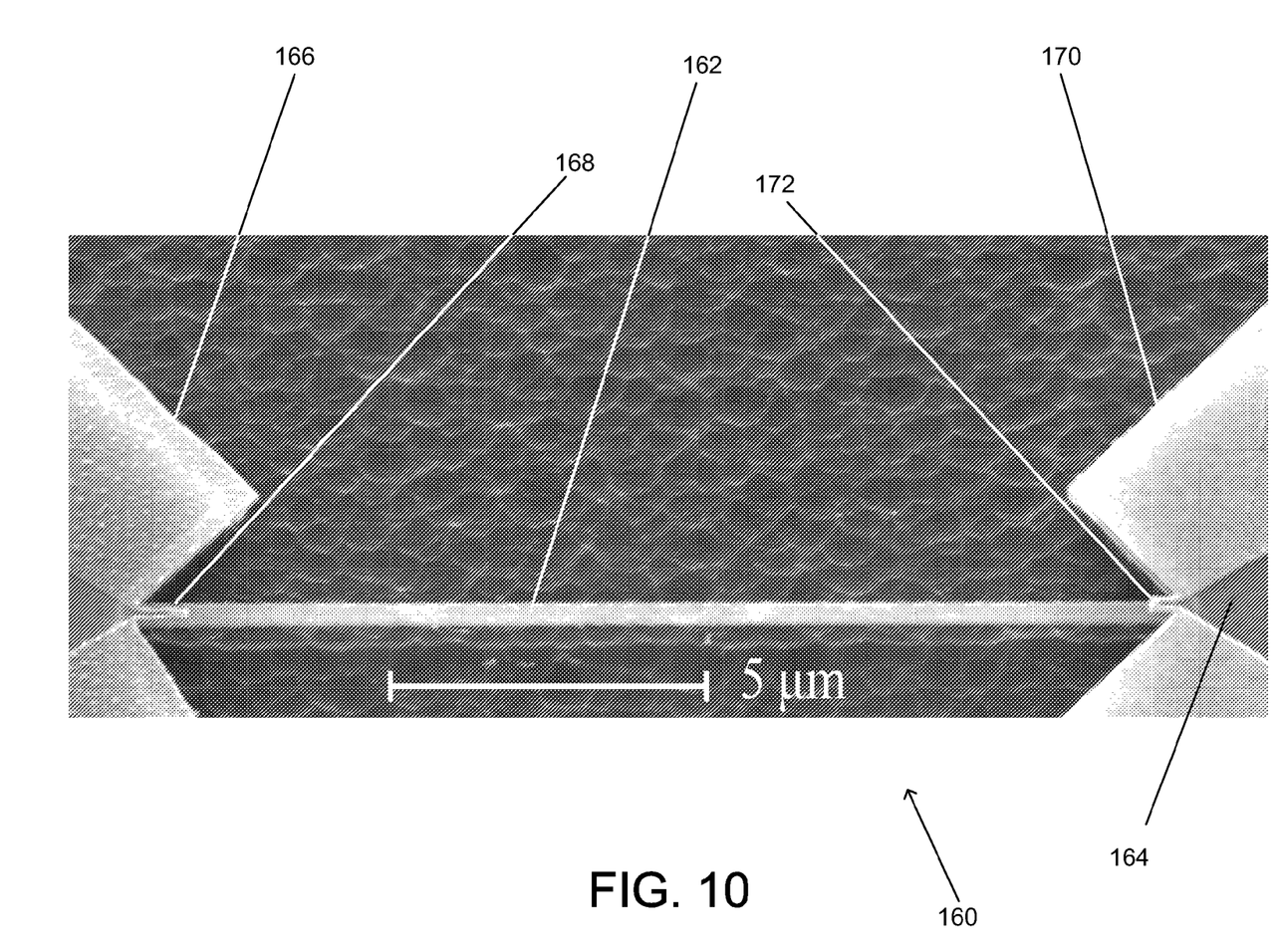
FIG. 10 is a scanning electron microscope image of a piezoresistive sensor that includes a thermally actuated doubly-clamped piezoresistive beam in accordance with an embodiment of the invention.

The thermal actuation techniques described above can also be used to excite oscillation in doubly-clamped beams. FIG. 10 is a scanning electron microscope photograph of a piezoresistive sensor including a bi-layer doubly-clamped beam in accordance with an embodiment of the invention. The photograph 160 shows a piezoresistive sensor including a beam 162 attached at each end to one or more substrates 164. A first circuit trace 166 is formed on the substrate and includes a loop 168 that extends onto one end of the beam. A second circuit trace 170 is formed on the substrate and includes a second loop 172 that extends onto the other end of the beam.

Figure 11:
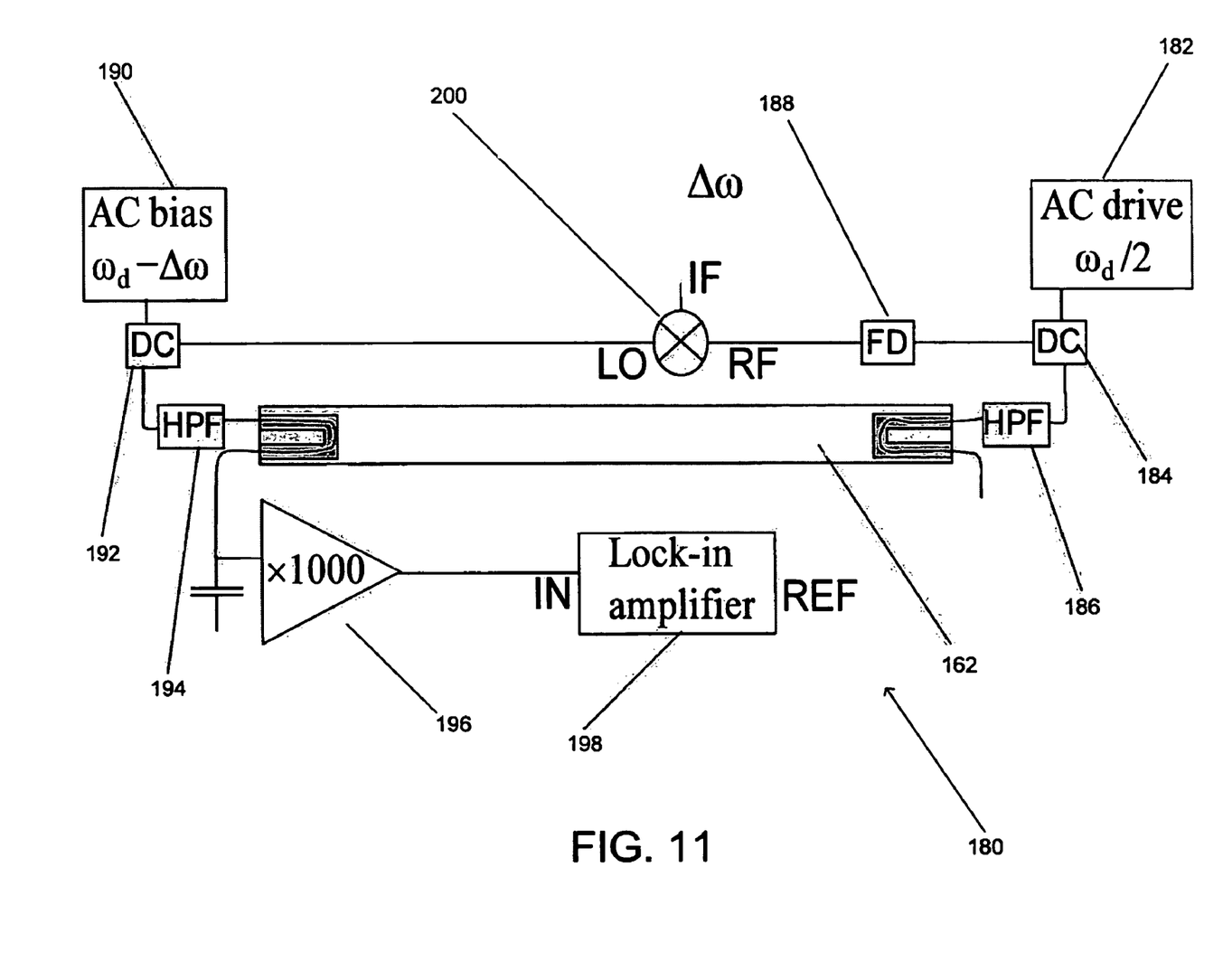
FIG. 11 is an equivalent electrical circuit of a piezoresistive sensor that uses an AC electrical signal to thermally actuate a doubly-clamped piezoresistive beam in accordance with an embodiment of the invention.

Circuitry that can be used to drive a doubly-clamped beam and perform downmixing detection of actuation of the doubly-clamped beam in accordance with an embodiment of the invention is shown in FIG. 11. The circuitry 180 includes an AC drive 182 that is connected via a directional coupler (DC) 184. The DC is connected to a High Pass Filter (HPF) 186 and a broadband frequency doubler (FD) 188. The output of the HPF is connected via the actuation loop at one end of the doubly-clamped beam 162 to ground. An AC bias source 190 is connected to a DC 192, which is connected to a HPF 194 and a mixer 200. The output of the HPF 194 is provided to the detection loop at the other end of the doubly-clamped beam. A pre-amplifier 196 detects current passing through the detection loop and provides it as an input to a lock-in amplifier 198. Fractions of the drive and bias signals are split off by the DCs 184, 192 and fed to the FD 188 and mixer 200 to produce the reference signal for the lock in amplifier.

In the illustrated embodiment, the AC drive signal provides an actuating current at one end of the doubly-clamped beam. The signal supplied at the other end of the doubly clamped beam is used in combination with the pre-amplifier 196 and the lock-in amplifier 198 to detect the actuation of the beam. In one embodiment, the actuation signal has a frequency $\omega_d/2$ and the bias signal has a frequency $\omega_d-\Delta\omega$. The actuation signal drives the cantilever at frequency $\omega_d$ and the piezoresistor in the detection circuit downmixes the bias signal to a frequency $\Delta\omega$.

Figure 12:
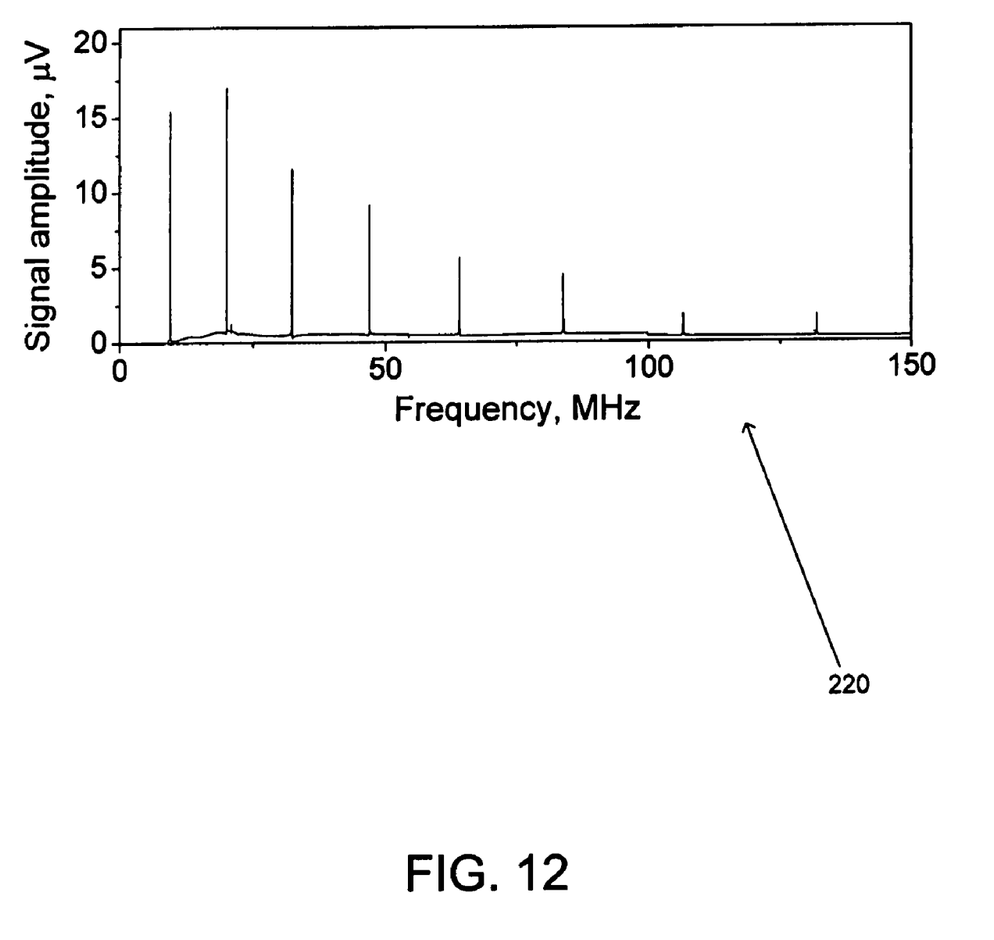
FIG. 12 is a chart illustrating the relationship between the frequency of an AC signal applied to a drive line to actuate a doubly-clamped piezoresistive beam and the amplitude of a signal generated by a transducer configured to detect variations in the resistance of piezoresistive materials used in the construction of the doubly-clamped beam.

A chart showing the raw signal from a 16 μm long beam detected as both the drive and vias voltages are swept over a very wide range of frequencies while keeping the down mixed frequency constant at 95 kHz is shown in FIG. 12. The large peaks correspond to the first eight out-of-plane flexural modes of the beam. The small peak near the second large peak corresponds to the first in-plane mode. On resonance, both quadratures of the lock-in signal fit the Lorentzian curve shape very well. The noise floor of 3 $nV/Hz^{1/2}$ is largely due to the Johnson noise of the piezoresistor. The small background signal originates from the parasitic coupling between bias, drive, and detection channels and the slight nonlinearity of the piezoresistor and pre-amplifier response.

In-Plane Resonance Modes

The devices described above utilize out-of-plane resonance modes. Many embodiments of the invention use thermal actuation to excite in-plane modes of vibration in asymmetric devices. The combination of high quality factor in viscous environments, such as air, and high surface-to-volume ratio of in-plane resonators can makes piezoresistive sensors that utilize such resonators particularly appropriate for gas sensing applications.

Figure 13:
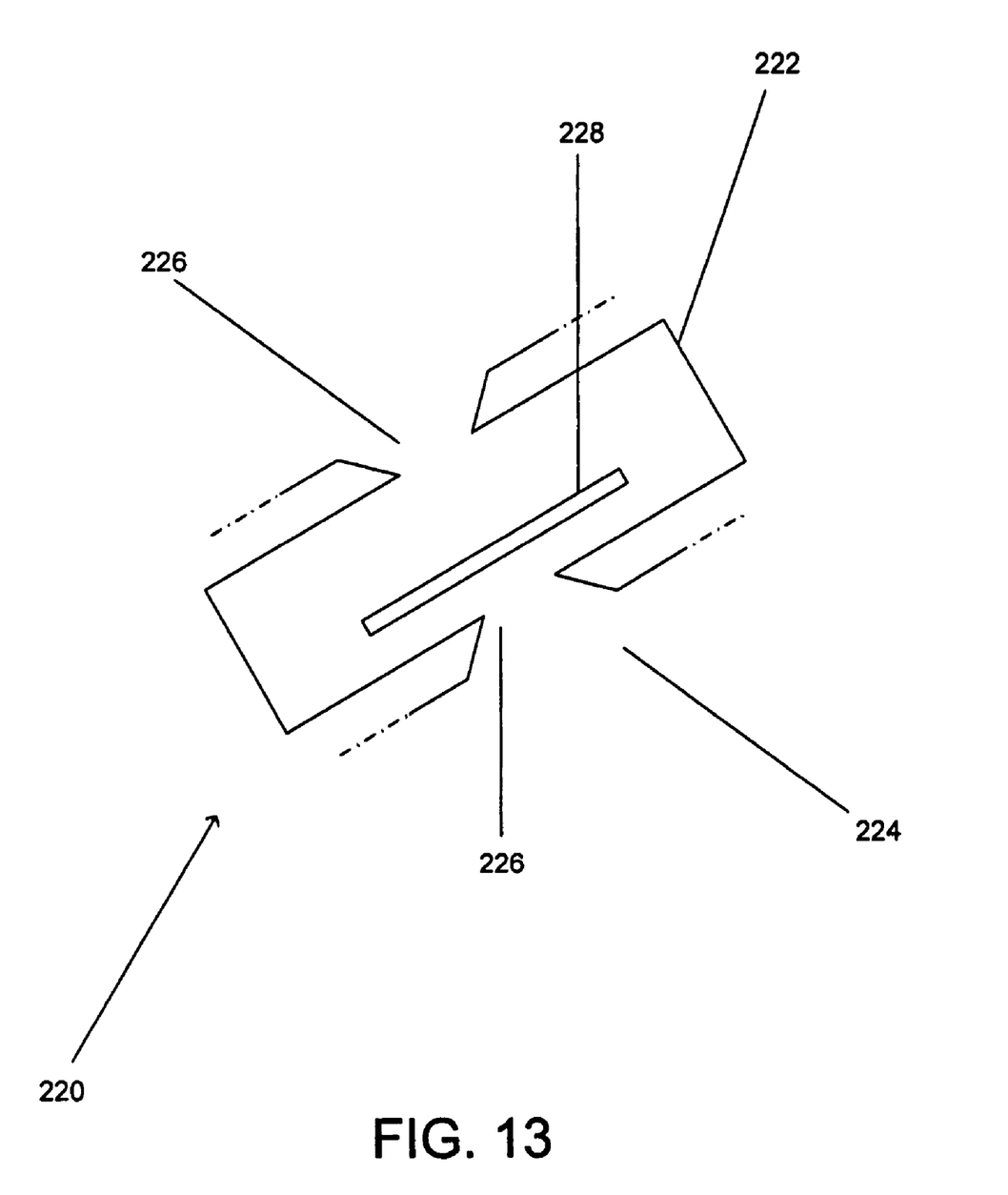
FIG. 13 illustrates a top view of a piezoresistive sensor that includes a resonator that can be excited to in plane modes of oscillation by thermal actuation.

An embodiment of a piezoresistive sensor in accordance with an embodiment of the invention that can use thermal actuation to excite in-plane modes of vibration is shown in FIG. 13. The piezoresistive sensor 220 includes a beam 222 that is connected to a substrate 224 via a pair of springs 226. In the illustrated embodiment, the springs are located at the midpoint of the long edge of a rectangular beam. A beam 222 includes a thin channel 228. In the illustrated embodiment, the channel is rectangular and is located asymmetrically with respect to the width of the beam. In other embodiments, the channel can be formed with a different shape and located elsewhere in an asymmetric manner with respect to the dimensions of the beam.

When a current is passed through the beam 222 via the springs 226, the generated heat is concentrated in the thing channel and this part of the beam expands more than the rest of the beam. In many instances the differences in the expansion results in the in plane bending of the beam and application of an oscillating actuation signal in the manner outlined above can be used to excite the in plane resonant mode of the beam. The piezoresistive materials used in the construction of the beam can also be used to detect the actuation of the beam using techniques similar to those outlined above.

In-plane resonators similar to the resonator shown in FIG. 13 can be realized by either using a thin metal film on a thin structural semiconductor layer, similar to the bi-layer structures described above with respect to out-of-plane resonators (for example using gold on silicon nitride), or by making the resonator entirely out of a thin metal film.

While the above description contains many specific embodiments of the invention, these should not be construed as limitations on the scope of the invention, but rather as an example of one embodiment thereof. For example, thermal actuation can be used in conjunction with techniques other than the use of piezoresistors for the detection of NEMS displacement. In many embodiments, thermal actuation is used in conjunction with detection techniques including, but not limited to, capacitive detection, magnetic detection and piezoelectric detection. In addition, the applications of piezoelectric sensors including NEMS resonators in accordance with embodiments of the invention are not limited to those described above and can include mass sensing of individual particles, both in vacuum and fluids, including sensing of biological structures (proteins, viruses, cells etc.), gas concentration sensing, including sensing of chemical warfare agents and sensing of volatile organic compounds in breath for medical applications, ultrafast AFM imaging (electrothermal actuation has been demonstrated to work at frequencies up to 1 GHz, far exceeding the operational range of the currently used AFM piezo shakers) and the construction of NEMS oscillators/clocks. Accordingly, the scope of the invention should be determined not by the embodiments illustrated, but by the appended claims and their equivalents.

What is claimed is:

1. A piezoresistive sensor, comprising:
a substrate;
a nanoelectromechanical cantilever connected to the substrate in at least one location;
a current path defined proximate the cantilever;
a signal source connected via circuitry to the current path; and
wherein the signal source is configured to provide a signal to thermally actuate a resonant mode in the cantilever.

2. The piezoresistive sensor of claim 1, wherein the nanoelectromechanical cantilever is a bi-layer cantilever.

3. The piezoresistive sensor of claim 2, wherein the bi-layer cantilever comprises:
a base layer; and
a piezoresistive layer formed on the surface of the base layer.

4. The piezoresistive sensor of claim 3, wherein one end of the bi-layer cantilever is connected to the substrate via a first cantilever leg and a second cantilever leg.

5. The piezoresistive sensor of claim 4, wherein the base layer is silicon and the piezoresistive layer is p-doped silicon.

6. The piezoresistive sensor of claim 2, wherein the bi-layer cantilever comprises:
a base layer; and
a metallic circuit trace formed on the base layer, which forms part of the current path.

7. The piezoresistive sensor of claim 6, further comprising detection circuitry configured to detect variations in the resistance of the metallic circuit trace.

8. The piezoresistive sensor of claim 6, wherein the base layer includes silicon carbide and the circuit trace includes metallic gold.

9. The piezoresistive sensor of claim 3, wherein the current path includes the piezoresistive layer of the bi-layer cantilever.

10. The piezoresistive sensor of claim 9, wherein:
each of the first and second cantilever legs comprises:
   a base layer; and
   a piezoresistive layer formed on the surface of the base layer; and
the circuitry includes a pair of symmetric bias resistors that are connected between the signal source and the piezoresistive layer of the first and second cantilever legs.

11. The piezoresistive sensor of claim 9, further comprising detection circuitry configured to detect variations in the resistance of the piezoresistive layer of the bi-layer cantilever.

12. A piezoresistive sensor, comprising:
a doubly-clamped nanoelectromechanical beam;
a first current path formed on one end of the doubly-clamped beam; and
a signal source connected to the first current path via circuitry and configured to provide a signal to thermally actuate a resonant mode in the doubly-clamped beam.

13. The piezoresistive sensor of claim 12, wherein the doubly clamed beam comprises:
a base layer;
a first metallic circuit trace formed on the surface of the base layer at one end of the doubly-clamped beam, which forms part of the first current path; and
a second metallic circuit trace formed on the surface of the base layer at the other end of the doubly-clamped beam, which forms part of a second current path.

14. The piezoresistive sensor of claim 13, further comprising detection circuitry connected to the second current path and configured to detect actuation of the beam using downmixing detection.

15. The piezoresistive sensor of claim 13, wherein the base layer includes silicon carbide and the metallic circuit traces include metallic gold.

16. A piezoresistive sensor, comprising
a substrate;
a beam that includes a channel, where the beam is connected to the substrate by at least two springs;
a current path passing through the beam; and
a signal source connected to the current path via circuitry and configured to provide a signal to thermally actuate a resonant mode in the beam.

17. The piezoresistive sensor of claim 16, wherein the beam is constructed from a base layer and a metallic surface layer.

18. The piezoresistive sensor of claim 17, wherein the base layer includes silicon nitride and the metallic surface layer includes metallic gold.

19. The piezoresistive sensor of claim 16, wherein the beam is formed from a thin layer of metal.

20. A piezoresistive sensor, comprising:
a nanoelectromechanical resonator connected in at least one location to a substrate;
an electrically conductive path formed on the resonator; and
a signal source connected to the electrically conductive path and configured to provide a signal to thermally actuate a resonant mode in the resonator.

21. The piezoresistive sensor of claim 20, wherein the nanoelectromechanical resonator is a bi-layer cantilever.

22. The piezoresistive sensor of claim 20, wherein the nanoelectromechanical resonator is a doubly-clamped beam.

23. The piezoresistive sensor of claim 20, wherein the nanoelectromechanical resonator is a beam including a channel connected to the substrate in two locations.

* * * * *